(12) United States Patent
Sorensen et al.

(10) Patent No.: US 6,642,280 B2
(45) Date of Patent: Nov. 4, 2003

(54) CONTROL SCHEME FOR CONVERSION OF VARIABLE COMPOSITION SYNTHESIS GAS TO LIQUID FUELS IN A SLURRY BUBBLE COLUMN REACTOR

(75) Inventors: James Christian Sorensen, Allentown, PA (US); Douglas Edward Benedict, Macungie, PA (US); Tsun-Chiu Robert Tsao, Allentown, PA (US); Joseph Klosek, Wescosville, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 80 days.

(21) Appl. No.: 09/925,233

(22) Filed: Aug. 9, 2001

(65) Prior Publication Data

US 2003/0039600 A1 Feb. 27, 2003

(51) Int. Cl.[7] .............................. C07C 27/00
(52) U.S. Cl. ............... 518/705; 518/700; 518/702; 518/704
(58) Field of Search ............... 518/705, 702, 518/704, 700

(56) References Cited

U.S. PATENT DOCUMENTS

| | | | |
|---|---|---|---|
| 4,546,111 A | * 10/1985 | Banquy | 518/703 |
| 4,888,130 A | 12/1989 | Banquy | 252/373 |
| 5,134,944 A | 8/1992 | Keller et al. | 110/234 |
| 5,266,281 A | 11/1993 | Kao et al. | 422/197 |
| 5,284,878 A | 2/1994 | Studer et al. | 518/700 |
| 5,348,982 A | * 9/1994 | Herbolzheimer et al. | 518/700 |
| 5,788,723 A | 8/1998 | Kiss | 48/197 |
| 6,063,355 A | 5/2000 | Fujimura et al. | 423/359 |

OTHER PUBLICATIONS

"*The LPMEOH™* " *Process–An Efficient Route to Methanol from Coal*, Roberts, et al, San Fran. Apr. 1985.
"*Methanol: Its Technology and Economics*," Chem. Engrg. Progress Symp. Series, vol. 66, 1970.
"Coproduction of Methanol Adds IGCC Flexibility," Modern Power Systems, Oct. 1997.

* cited by examiner

*Primary Examiner*—J. Parsa
(74) *Attorney, Agent, or Firm*—Robert J. Wolff

(57) ABSTRACT

A control scheme is set forth for conversion of variable composition synthesis gas to liquid fuels in a three-phase or slurry bubble column reactor (SBCR). The control scheme allows one to achieve constant or optimum liquid fuel production and constant or limited purge gas flow with highly variable synthesis gas feed condition. This is accomplished by adjusting one or more of the following independent variables: recycle ratio, water addition, and bypass flow.

6 Claims, 1 Drawing Sheet

CONTROL SCHEME FOR CONVERSION OF VARIABLE COMPOSITION SYNTHESIS GAS TO LIQUID FUELS IN A SLURRY BUBBLE COLUMN REACTOR

BACKGROUND OF THE INVENTION

Conventional liquid fuels synthesis (e.g. methanol synthesis) is conducted in gas phase, fixed-bed reactors and requires carefully controlled synthesis gas feed composition and flow. (See for example Roberts, G. W., et al, "The LPMEOH™ Process: An Efficient Route to Methanol from Coal," Conference on Coal Gasification and Synthetic Fuels for Power Generation, San Francisco, Apr.14–18, 1985; see also Strelzoff, S., "Methanol: Its Technology and Economics," Methanol Technology and Economics, Chemical Engineering Progress Symposium Series, No. 98, Vol. 66, AIChE, 1970.) This is because the liquid fuel synthesis reactions are generally highly exothermic, and the synthesis catalyst is generally very temperature sensitive. The catalyst loses its activity at high temperature. Furthermore, the equilibrium conversion of synthesis gas to a liquid fuel is higher at lower temperatures.

Therefore, the key consideration in designing a conventional liquid fuel synthesis reactor (also known as a slurry bubble column reactor or SBCR) is removal of the heat of reaction and maintaining operation in a specific temperature range, namely 428–518° F. (220–270° C.) for methanol. Isothermal operation at about 482° F. is the optimum condition for methanol. Since synthesis gas feed composition and flow affect the reaction temperature, they are strongly controlled and normally held constant. Variations, especially rapid changes, are not well tolerated by the conventional gas phase, fixed-bed reactors. The heat of reaction is removed by either cold gas quenching (injection of cold synthesis gas along the length of the reactor) or production of steam (catalyst in tubes, boiling water on shell-side).

Gas phase methanol synthesis based on synthesis gas derived from gasification is commercially practiced. (See for example U.S. Pat. Nos. 4,888,1301; 5,266,281 and 5,284,878; see also Osterstock, E. R., et al, "Coproduction of Methanol Adds IGCC Flexibility," Modern Power Systems, October 1997.) The synthesis gas feed composition and flow are carefully controlled per the considerations above. Normally, the synthesis gas feed composition is adjusted to be stoichiometrically "balanced" (i.e. the ratio $[H_2$ minus $CO_2]/[CO$ plus $CO_2]$ equals 2.0) or is $H_2$-rich (i.e. this ratio is greater than 2.0).

In contrast to gas phase methanol synthesis, synthesis of methanol in a slurry bubble column reactor (SBCR) is a fundamentally different technology and more suitable for non-stoichiometric, variable synthesis gas feed composition and flow, including CO-rich synthesis gas feed. This is because the catalyst is slurried in an inert mineral oil that acts as a sink for heat removal. The large heat sink greatly eases temperature control, allowing essentially isothermal operation. Moreover, the liquid phase medium is highly robust and tolerant to wide-ranging and rapid changes in gas feed condition.

The objective of the present invention is to insure reliable product (especially a liquid fuel product but also including a gaseous product and/or a product that has a chemical use) production and limited purge gas flow when processing highly variable gas feed in a SBCR. Waste gasification art in general does not deal with tight control of downstream product and purge gas at fixed rates when the waste composition and flow vary over a wide range. "Waste" here is meant to be heterogeneous, carbonaceous material that has low or negative value like municipal solid waste, refuse-derived fuel, industrial solid or liquid waste, sewage sludge, biomass waste, hazardous waste, toxic waste, refinery sludge or slop, plastic waste, automobile shredder waste, contaminated aqueous solutions, etc.

U.S. Pat. No. 5,788,723 (7) describes a process for the high temperature gasification of heterogeneous waste. The focus is on maintaining complete gasification in the face of varying heterogeneous feedstock character by controlling the oxygen lance operation. This patent does not address downstream needs.

U.S. Pat. No. 6,063,355 (8) describes a method and apparatus for treating wastes by gasification, and also the problem with changes in the quality of low-calorific value wastes when producing a downstream synthesis product, in this case ammonia. The invention solves the problem by adding a supplemental fuel having a high calorific value, like coal or coke, such that the mixed feedstock has a stable quality and quantity. This is an expensive solution, for ammonia or methanol production, and is totally different from the proposed concept.

U.S. Pat. No. 5,134,944 (9) describes, "processes and means for waste resources utilization." Solid waste material is gasified and multiple products produced, including methanol, such that there are no remaining disposal problems. A key aspect of the invention is the use of a supplemental particulate carbon fuel like coal. The invention does not address the dynamics and needs of the downstream operation. This invention is totally different from the proposed concept.

International Patent Application WO 00/30973 (10) describes a gasification proves for making ammonia from heterogeneous waste feedstock. The invention does not attempt to maintain constant or optimum ammonia product flow and constant or limited purge gas flow.

BRIEF SUMMARY OF THE INVENTION

The present invention is a control scheme for conversion of variable composition synthesis gas to a product (especially, but not limited to, a liquid fuels product such as methanol) in a three-phase or slurry bubble column reactor (SBCR). The control scheme allows one to achieve constant or optimum liquid fuel production and constant or limited purge gas flow with highly variable synthesis gas feed condition. This is accomplished by adjusting one or more of the following independent variables: recycle ratio, water addition, and bypass flow. The ability to achieve this control over a very wide range of synthesis gas feed condition is surprisingly strong given that only three variables are adjusted.

DETAILED DESCRIPTION OF THE INVENTION

Figure 1:
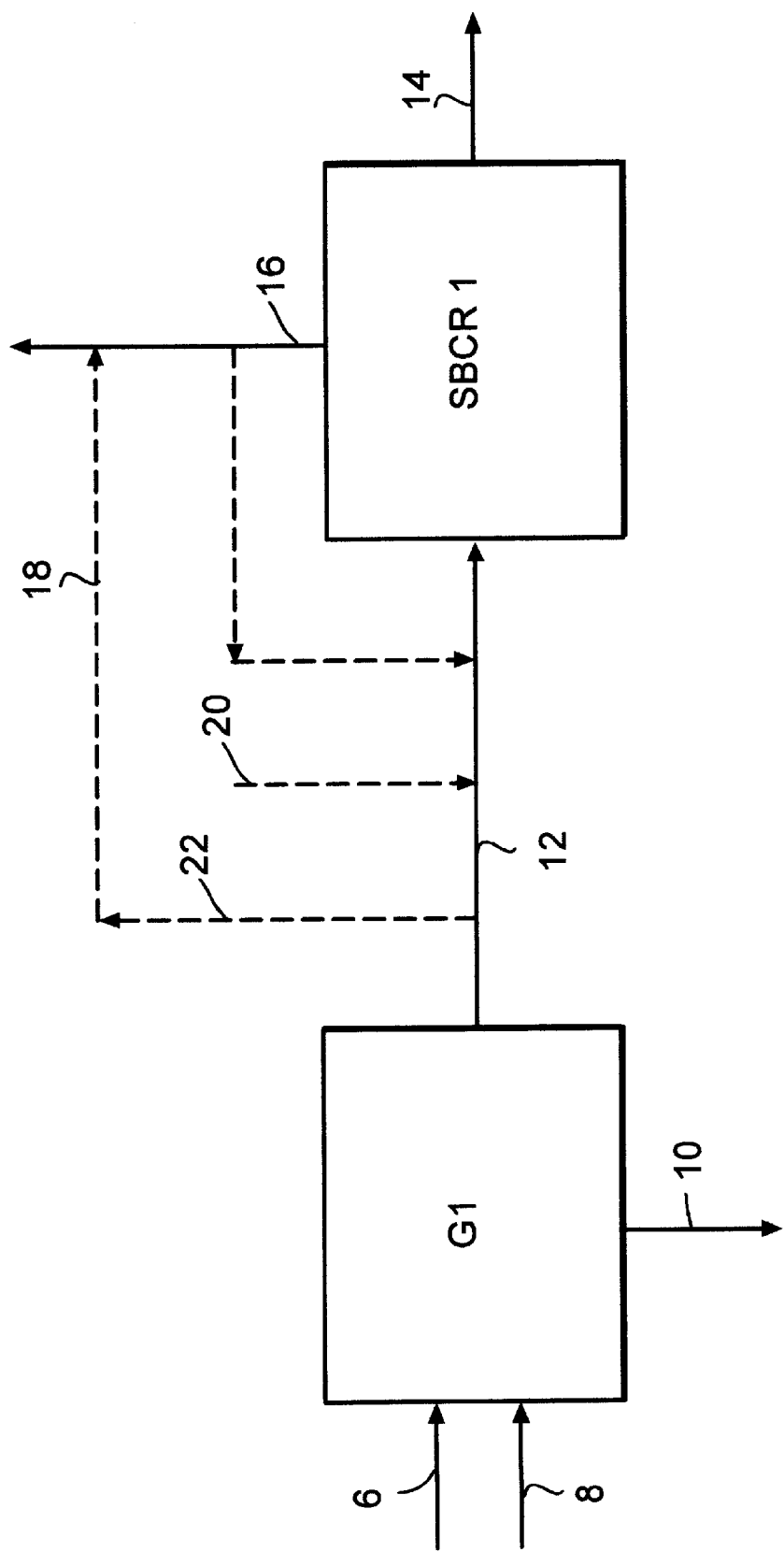
FIG. 1 is a schematic drawing of one embodiment of the present invention.

The process of the present invention is best illustrated with respect to a specific embodiment thereof such as FIG. 1's embodiment. Referring to FIG. 1, the present invention concerns a process which includes (but is not limited to) the following steps:

(a) converting, in a gasifier [G1], feed streams comprising a waste feedstock stream [stream 6] and an oxygen containing stream [stream 8] into at least one waste effluent stream [stream 10] and a synthesis gas stream [stream 12] comprising hydrogen and carbon monoxide wherein the waste feedstock stream has an oscillating composition, particularly with regard to its carbon content, resulting in an oscillating carbon to hydrogen ratio in the synthesis gas stream;

(b) converting, in a slurry bubble column reactor [SBCR1] containing a catalyst, the synthesis gas stream [stream 12] into a liquid fuel product stream [stream 14] and a purge gas stream [stream 16] wherein:

(1) a portion, if any, of the purge gas stream is recycled to the synthesis gas stream entering the SBCR as a purge gas recycle stream [stream 18];

(2) a water stream [stream 20] is added, if at all, to the synthesis gas stream entering the SBCR; and (3) a portion, if any, of the synthesis gas feed bypasses the SBCR as a synthesis gas bypass stream [stream 22] and is combined directly with the purge gas stream.

Applying the present invention to the above prior art process, the present invention is an improvement for achieving essentially constant or optimum production of the liquid fuel stream and essentially constant or limited production of the purge gas stream notwithstanding the synthesis gas feed stream's oscillating carbon to hydrogen ratio. The improvement comprises a control scheme responsive to said oscillating carbon to hydrogen ratio in the synthesis gas stream. The control scheme includes (but is not limited to) the following steps:

(i) increasing and/or commencing the flow in the purge gas recycle stream [stream 18] in step (b)(1) as the ratio goes up and decreasing and/or terminating the flow in the purge gas recycle stream in step (b)(1) as the ratio goes down; and/or (ii) increasing and/or commencing the flow in the water stream being added to the synthesis gas stream [stream 20] in step (b)(2) as the ratio goes up and decreasing and/or terminating the flow in the water stream being added to the synthesis gas stream in step (b)(2) as the ratio goes down; and/or (iii) decreasing and/or terminating the flow in the synthesis gas bypass stream [stream 22] in step (b)(3) as the ratio goes up and increasing and/or commencing the flow in the synthesis gas bypass stream in step (b)(3) as the ratio goes down.

In one general embodiment of the present invention, a methanol synthesis catalyst (optionally in combination with a methanol dehydration catalyst) is utilized and the product stream contains primarily methanol (and/or dimethyl ether if methanol dehydration catalyst utilized).

In another general embodiment, an iron or cobalt based catalyst is utilized and the product stream contains primarily Fischer-Tropsch products. In this case, the equilibrium constraints of the methanol synthesis reaction are not present and control is easier.

The benefit of the present invention is illustrated using a set of hypothetical synthesis feed gas conditions provided to a slurry bubble column reactor (SBCR) of fixed design for producing methanol.

Table 1 defines three fresh synthesis gas feed compositions that represent a very wide range of gasification variability.

TABLE 1

Variable Fresh Synthesis Gas Feed Definition (all at 750 psia)

| | Feed Synthesis gas Conditions: | | |
|---|---|---|---|
| | Case 1, Base Case | Case 2, CO-Rich Gas | Case 3, H$_2$-Rich Gas |
| Composition, mole % | | | |
| H$_2$ | 45.0 | 30.0 | 60.0 |
| CO | 45.0 | 60.0 | 30.0 |
| CO$_2$ | 5.0 | 5.0 | 5.0 |
| N$_2$/Ar | 5.0 | 5.0 | 5.0 |
| Total | 100.0 | 100.0 | 100.0 |
| H$_2$/CO Ratio | 1.0 | 0.5 | 2.0 |
| Feed Flow, lb moles/hr | 1,000 | 1,000 | 1,000 |
| Feed Flow LHV, MMBtu/hr | 101.7 | 104.1 | 98.8 |

Case 1 is defined as the base case condition, with the H$_2$/CO ratio equal to 1:1. For exemplary purposes, this is considered the "normal" process condition, representing the average waste feedstock character to gasification. Case 2 represents a swing to CO-rich synthesis gas, with the H$_2$/CO ratio decreased to 0.5. This represents a change in the waste feed to a more carbon-rich character relative to the average specification. Case 3 represents the opposite swing, to a H$_2$-rich synthesis gas, with the H$_2$/CO ratio increased to 2.0. This represents a change in the waste feed character to a carbon-lean specification, relative to the average specification. Changes in synthesis gas condition can also be caused by off-operation of the gasifier. The range of variation cited is very large for a fixed design.

For exemplary purposes, the base case (Case 1) design conversion of fresh synthesis gas feed is specified to be 40.0% using a lower heating value (LHV) conversion ([Btu's in minus Btu's out]/Btu's in). For the 1,000 lb moles/hr of gas feed flow in Table 1, this sets the Case 1 methanol production at 122 lb moles/hr and the fuel gas purge at 61.0 MMBtu/hr LHV. In commercial operation, it is desired that the methanol production be maintained constant (when sufficient synthesis gas feed is available) and that the purge gas flow (the Btu's) be limited to the base case flow. The desired/ideal control would maintain the product streams nominally within about 5% of the base case flows. Given these commercial targets, Cases 2 and 3 represent very challenging variations in the feed condition.

Synthesis of methanol in a slurry bubble column reactor (SBCR) was simulated using a computer model that describes the thermodynamic, kinetic, and hydrodynamic performance of the SBCR. The base case design specification was achieved with the SBCR operating at 482° F. (250° C.), 750 psia, with a catalyst slurry concentration of 45 weight % (wt % copper-zinc catalyst solids in mineral oil-catalyst slurry, solids calculated on oxide basis), a recycle ratio of 0.5 (recycle gas molar flow rate/fresh synthesis gas feed molar flow rate), and a space velocity of 4,500 liters/hr-kg (standard liters of feed gas at 0° C., 1 atm; kg catalyst on oxide basis). The resultant calculated methanol production is 122 lb mole/hr and the fuel gas purge is 61.0 MMBtu/hr LHV.

The present invention is illustrated with Cases 2 and 3. The SBCR size is fixed by the base case. Table 2 summarizes the control measures and results for the base case (Case 1) and Cases 2 and 3 described below.

TABLE 2

Control Measures and Results

|  | Case 1<br>Base<br>Case | Case 2<br>CO-Rich<br>Gas | Case 3<br>$H_2$-Rich<br>Gas | Case 3A<br>$H_2$-Rich<br>Gas |
|---|---|---|---|---|
| Control Measures: | | | | |
| Recycle Ratio | 0.5 | 2.0 | 0.0 | 0.5 |
| Water Addition, lb moles/hr | 0 | 200 | 0 | 0 |
| Bypass Flow, lb moles/hr | 0 | 0 | 0 | 300 |
| Results: | | | | |
| Space Velocity, liters/hr-kg | 4,500 | 9,000 | 3,000 | 3,150 |
| % Conversion | 40.0 | 41.4 | 39.3 | 55.9 |
| Methanol Production Rate, lb moles/hr | 122 | 123 | 118 | 116 |
| Fuel Gas Purge Rate, MMBtu/hr LHV | 61.0 | 61.0 | 60.0 | 60.1 |

With Case 2 operation on CO-rich gas, the recycle ratio is increased to 2.0, and water is added to the reactor feed at the rate of 200 lb moles/hr. The water effects the water-gas shift reaction and increases the $H_2$/CO ratio within the SBCR, enhancing methanol production. The resultant space velocity for the fixed reactor design is 9,000 liters/hr-kg. The resultant methanol production is 123 lb mole/hr and the purge gas flow is 61.0 MMBtu/hr LHV. Thus, the control measures satisfy the commercial performance target discussed above.

With Case 3 operation on $H_2$-rich gas, the recycle ratio is reduced to zero. There is no water addition. The resultant space velocity for the fixed reactor design is 3,000 liters/hr-kg. The resultant methanol production is 118 lb mole/hr and the fuel gas purge flow is 60.0 MMBtu/hr LHV. The control measures again satisfy the commercial performance target discussed above.

As an alternative to the Case 3 control described above, bypass of fresh synthesis gas feed can be used. This is illustrated by Case 3A: with Case 3A operation, 300 lb moles/hr of fresh synthesis gas feed are bypassed, and the recycle ratio is set to 0.5. The resultant space velocity for the fixed reactor design is 3,150 liters/hr-kg. The resultant methanol production is 116 lb moles/hr and the fuel gas purge is 60.1 MMBtu/hr LHV. Once again, the control measures satisfy the commercial performance target.

Over the range of cases illustrated, the methanol production rate and purge gas rate are controlled within 5% of the base case. This is surprisingly effective control, given only three variables to adjust (all within the SBCR methanol process) and the very wide range of feed variation.

One also has the ability to control the SBCR reactor temperature and pressure in FIG. 1. These variables can be used to assist with optimizing operation with variable fresh synthesis gas feed; however, temperature is not a parameter of sufficient range to have a significant impact, and pressure variation is a very complicated approach to control. In principle, catalyst slurry concentration and slurry inventory can also be varied for control, but this is impractical for the rapidly changing dynamic situations of interest.

The present invention has been described with reference to FIG. 1's embodiment thereof. The skilled practitioner will appreciate that there are many other embodiments of the present invention that are within the scope of the following claims.

What is claimed is:

1. In a process comprising converting, in a slurry bubble column reactor containing a catalyst, a synthesis gas stream comprising hydrogen and carbon monoxide into a product stream and a purge gas stream wherein:

(1) a portion, if any, of the purge gas stream is recycled to the synthesis gas stream entering the SBCR as a purge gas recycle stream;

(2) a water stream is added, if at all, to the synthesis gas stream entering the SBCR;

(3) a portion, if any, of the synthesis gas feed bypasses the SBCR as a synthesis gas bypass stream and is combined directly with the purge gas stream; and (4) the synthesis gas stream has an oscillating carbon to hydrogen ratio;

the improvement comprising a control scheme responsive to said oscillating carbon to hydrogen ratio in the synthesis gas stream, said control scheme comprising:

(i) increasing or commencing the flow in the purge gas recycle stream in step (1) as the ratio goes up and decreasing or terminating the flow in the purge gas recycle stream in step (1) as the ratio goes down; and/or (ii) increasing or commencing the flow in the water stream being added to the synthesis gas stream in step (2) as the ratio goes up and decreasing and/or terminating the flow in the water stream being added to the synthesis gas stream in step (2) as the ratio goes down; and/or (iii) decreasing or terminating the flow in the synthesis gas bypass stream in step (3) as the ratio goes up and increasing or commencing the flow in the synthesis gas bypass stream in step (3) as the ratio goes down.

2. The process of claim 1 where the product stream is a liquid fuel product stream.

3. The process of claim 1 where the product stream is a gaseous product stream.

4. The process of claim 1 where the product stream has a chemical use.

5. The process of claim 1 wherein the product stream contains primarily methanol and/or dimethyl ether.

6. The process of claim 1 where liquid fuel product stream contains primarily Fischer-Tropsch products.

* * * * *